United States Patent [19]
Blezard et al.

[11] Patent Number: 5,498,791
[45] Date of Patent: Mar. 12, 1996

[54] NITROSAMINE & NITRITE INHIBITION

[75] Inventors: Michael Blezard; Glyn R. Jones, both of Whitehaven; Moharam Ghadimi, Milton Keynes, all of England

[73] Assignee: Albright & Wilson, Limited, Warley, England

[21] Appl. No.: 376,040

[22] Filed: Jan. 20, 1995

Related U.S. Application Data

[62] Division of Ser. No. 11,976, Feb. 1, 1993, Pat. No. 5,442,113.

[30] Foreign Application Priority Data

Jan. 31, 1992 [GB] United Kingdom .................... 9202057

[51] Int. Cl.⁶ .................................................. C07C 209/90
[52] U.S. Cl. .............................. 564/2; 252/526; 252/528; 252/545; 544/173; 546/347; 548/341.1; 560/2; 564/4; 564/6; 564/160; 564/198; 564/297; 564/298; 564/299

[58] Field of Search ..................... 564/2, 6, 160, 564/198, 297, 298, 299, 4; 544/173; 546/347; 548/341.1; 560/2; 252/526, 528, 545

[56] References Cited

FOREIGN PATENT DOCUMENTS 0105556  4/1984  European Pat. Off. .

*Primary Examiner*—Peter O'Sullivan
*Attorney, Agent, or Firm*—Frishauf, Holtz, Goodman, Langer & Chick

[57] ABSTRACT

A synergistic mixture of a carbonate and/or bicarbonate with a phosphonate, especially an organoamino methylene phosphonate or an N-oxide thereof, inhibits or reduces nitrosamine contamination during preparation, storage and/or heating of products which are susceptible to contamination with nitrosamine.

20 Claims, No Drawings

NITROSAMINE & NITRITE INHIBITION

This is a division of application Ser. No. 08/011,976 filed Feb. 1, 1993, now U.S. Pat. No. 5,442,113.

The present invention relates to a method of inhibiting the formation of nitrosamines and nitrites, especially during the preparation and/or storage of amine oxides, an amine oxide composition containing a stabiliser and an improved process for the preparation of tertiary amine oxides.

Amine oxides are conventionally prepared by reacting a tertiary amine with hydrogen peroxide. In order to complete the reaction within a commercially acceptable time it is necessary to heat the reaction mixture and/or to employ a catalyst. Since excessive heating tends to cause (or accelerate) the decomposition of peroxide, the use of a catalyst is preferred.

It has been suggested, e.g. in U.S. Pat. No. 3,333,000 that a mixture comprising sodium bicarbonate in concentrations of from 0.02 to 2% by weight of the amine together with sodium pyrophosphate will catalyse the reaction. In practice, concentrations of bicarbonate in the lower part of the range, i.e. below 1% by weight of the amine were found sufficient to catalyse the reaction and higher concentrations were avoided, so as not to leave any substantial residue of bicarbonate in the product.

Subsequently it has been found that carbon dioxide is a very effective catalyst and its use has now replaced that of sodium bicarbonate (see, for instance, GB 2 032 422, FR 2 632 638 or U.S. Pat. No. 4 247 480).

EP 0 409 043 described the use of certain aminophosphonates as catalysts in the preparation of amine oxides.

It has been recognised for some years that nitrosamines, which are widely regarded as being potentially harmful, and nitrites, which may be precursors of nitrosamines are commonly present as minor, but undesirable, trace contaminants of amine oxides. These contaminants are conventionally present in commercial amine oxides at very low levels of between 200 and 1000 parts per billion.

Until recently, such levels have been at or below the limits of detection. However, improved analytical methods, for instance based on chemiluminescence, have now made it possible to detect total nitrosamine and nitrite (referred to herein as "total NO") down to 10 parts per billion, or lower. This is considerably less than normal ambient atmospheric levels.

There is now a pressing demand for products containing less than 50 ppb total NO. It is likely that lower levels still would be demanded if they were thought to be achievable. It is an object of our invention to provide amine oxide products containing less than 50 ppb total NO preferably less than 20 ppb and most preferably less than 10 ppb.

A particular problem arises because nitrosamine levels, even in products prepared containing low initial concentrations of total NO, have been found to increase during aging especially at elevated temperatures. A particular object of the invention is therefore to stabilise amine oxides so as to maintain the aforesaid low levels of total NO during storage.

It has been found possible, in theory, to obtain very low levels of total NO by controlling the ratio of peroxide to amine and using highly pure reagents and process water which exclude dissolved polyvalent metal ions. However, the conditions are so sensitive that it is not possible in industrial practice to obtain consistently low total NO levels by this approach. The products moreover are not stabilised against the accumulation of NO on storage.

GB 2 252 320 describes the use of relatively high concentrations of carbonates and/or bicarbonates (greater than 2.5% by weight of the amine) to inhibit the formation of nitrosamines, both initially during the oxidation of amines and, subsequently, to stabilise the product. However, to achieve consistently low levels of total NO using bicarbonates, the amount of bicarbonate required may result in levels of inorganic impurity in the product which are unacceptable to some customers.

We have now discovered that bicarbonates and/or carbonates are synergistic with phosphonates such as organoamino methylene phosphonates, and their oxides, in inhibiting the formation of nitrosamines and nitrites during the preparation and/or storage of amine oxides. They may in some circumstances assist in lowering the nitrosamine content of a previously contaminated sample.

The present invention provides the use of a synergistic mixture of a carbonate and/or bicarbonate with a phosphonate to inhibit or to reduce nitrosamine contamination in products which are susceptible to contamination with nitrosamine.

The present invention further provides a method of stabilising an amine oxide in order to inhibit the formation of nitrosamines and nitrites during preparation, storage and/or heating by adding thereto a synergistic stabiliser comprising:

(i) from 0.05% to 20% by weight (based on the weight of amine used to prepare the amine oxide) of a bicarbonate and/or a carbonate; and (ii) from 0.005% to 5% by weight (based on the weight of amine used to prepare the amine oxide) of a phosphonic acid or its salts, in which (i) and (ii) are added either separately or together to the amine oxide before, during or after the preparation thereof.

The present invention also provides a composition comprising an amine oxide and a synergistic stabiliser comprising from 0.05% to 20% by weight (based on the weight of amine used to prepare the amine oxide) of a bicarbonate and/or a carbonate and from 0.005% to 5% by weight (based on the weight of amine used to prepare the amine oxide) of a phosphonic acid or a salt thereof.

The present invention further provides a method for the preparation of an amine oxide which comprises reacting a tertiary amine with hydrogen peroxide in the presence of a synergistic stabiliser comprising an amount greater than 0.05% by weight (based on the weight of the amine) of a bicarbonate and/or a carbonate and an amount greater than 0.005% by weight of an alkylamino phosphonate such as a polyalkylene amine methylene phosphonate, said amount being sufficient substantially to inhibit nitrosamine and nitrite formation.

The bicarbonate and/or carbonate component(i) may suitably comprise a bicarbonate such as sodium bicarbonate. Alternatively, other water soluble bicarbonates, e.g., alkali metal bicarbonates such as potassium bicarbonate or lithium bicarbonate, or alkaline earth metal bicarbonates such as magnesium or calcium bicarbonate may be present.

Preferably, component (i) may comprises a carbonate such as an alkali metal, alkaline earth metal or ammonium carbonate, e.g., sodium, magnesium or calcium carbonate, or a mixture of bicarbonate and carbonate, e.g., in a molar ratio of from 0.01:1 to 1:0.01 especially 1:1, provided that, if the carbonate is added to the reaction mixture, the pH is not high enough to cause significant decomposition of the hydrogen peroxide during the preparation of amine oxides. E.g. we prefer that the pH of the reaction mixture during the preparation of the amine oxide should be less than 10, preferably less than 9.8, typically less than 9.5. However, when the stabiliser is added to the product after preparation, such a constraint does not arise and therefore higher pH values may be tolerated depending on the desired end use. In a preferred embodiment, if carbonate and/or bicarbonate species are present in the reaction mixture but the pH of the mixture is carefully controlled, e.g. less than 10, more preferably less than 9.8, typically less than 9.5 for example by the use of dilute acids, excessive decomposition of the peroxide is avoided. Furthermore, at completion of the reaction when maintaining a weakly alkaline pH is not critical, the pH of the reaction mixture can be raised to promote the stability of the sample. We prefer the pH of the product to be raised by, for example an alkali or alkaline metal hydroxide solution, e.g. sodium hydroxide solution to a pH of 9.5–12.0, preferably 10–11.5, more preferably 10.3–11.2.

The phosphonate (ii) is preferably an organoamino methylene phosphonate of the formula $RR'—NCH_2PO_3M_2$, wherein: R and R' may each be separately selected from a $CH_2PO_3M_2$ group, a $C_{1-12}$, (preferably $C_{1-4}$) alkyl group, an amino, hydroxy, phosphono or carboxy substituted $C_{1-6}$ (preferably $C_{1-4}$) alkyl group, or a group of the formula $H[O(CH_2)_m]_n$ or $M_2O_3PCH_2 [NCH_2PO_3M_2(CH_2)_m]_n$; each M is hydrogen or a cation such that the composition is water soluble; and n is from 1 to 6 and each m is 2 to 6; or an N-oxide thereof.

Preferably R is a methylenephosphonate group and R' is a polyethyleneamino poly (methylenephosphonate) group, e.g. wherein n is from 1 to 5 preferably 2 to 4, or an ethylene or hydroxy ethylene group.

Where the amino phosphonate is added to the reaction mixture during the preparation of the amine oxide, the amino phosphonate stabiliser will normally be converted to the corresponding oxide in situ. Examples of suitable amino methylenephosphonate include sodium amino tris (methylenephosphonate), amino tris(methylenephosphonate) N-oxide or preferably sodium diethylenetriamine penta(methylenephosphonate) or sodium tetraethylenepentamine hepta(methylenephosphonate), available respectively as BRIQUEST 301-32S, BRIQUEST 3010-25s, BRIQUEST 543-25S and BRIQUEST 785-25S. (The word BRIQUEST is a Registered Trade Mark). We particularly prefer to use a combination of ethanolamine bis (methylenephosphonate) and diethylenetriamine penta(methylenephosphonate) the latter being added either with the former or after preparation.

Although we prefer that at least part of the synergistic stabilisers be present initially during the preparation of the amine oxide, it is possible to add some or all of the mixture, or of either component, during or after the preparation. In particular the poly(ethyleneamino) poly(methylenephosphonates) are especially effective for stabilising the product if added after the preparation.

The component (i) is preferably present in a total proportion of from 0.1 to 20% by weight based on the weight of amine used to prepare the product, preferably at least 0.5 e.g. at least 1% especially more than 2% in order to achieve effective catalysis and inhibition. We prefer that the proportion of carbonate be as low as possible consistent with adequate catalysis and inhibition in order to minimise inorganic impurities, i.e. less than 12%, preferably less than 8%, all percentages being based on the weight of amine used. An amount between 3% and 6.5%, based on the weight of amine used, has been found particularly suitable. Usually these concentrations will equate to a concentration of from 0.05 to 10% based on the total composition e.g. 0.1 to 5, especially 0.75 to 4%.

The component (ii) is typically present in an amount of from 0.005 to 10% by weight based on the weight of amine used, more preferably 0.05 to 5% e.g. 0.1 to 3% especially 0.2 to 2%.

The proportion by weight of (i) to (ii) is usually between 1:0.001 and 1:10, preferably. 1:0.01 to 1:2 especially 1:0.02 to 1:1 e.g. 1:0.05 to 1:0.5.

The preparation of the amine oxide is preferably carried out in a conventional manner by reacting a tertiary amine with aqueous hydrogen peroxide. The peroxide may be present in a substantially equimolar amount based on the amine or in a (preferably very small) stoichiometric excess, e.g. in ratio of 1:0.9, amine to peroxide, to 1:1.1. The excess of peroxide is preferably less than 0.05% based on the stoichiometric weight.

The amines that may be used in the process of our invention are typically amines of the general formula $R^1 R^2 R^3 N$, wherein $R^1$, $R^2$ and $R^3$ represent straight or branched chain alkyl groups, alkenyl groups or aralkyl groups which may be the same or different. They may be lower alkyl groups, i.e. of from 1 to 7, preferably 1 to 4, carbon atoms, but in a preferred embodiment of this invention, the tertiary amines may instead be represented by the general formula. $(R)_m (R^1)_n N$, wherein m=1 or 2 and n=(3-m).

The R groups, which may be the same or different, represent in this case $C_6$–$C_{24}$ alkyl or alkenyl groups, $C_{6-24}$ alkyl or alkenyl polyalkyleneoxy groups, $C_6$–$C_{23}$ esteralkyl or ester alkenyl groups, amidoalkyl or amidoalkenyl groups, and the $R^1$ groups, which may also be the same or different, represent $C_1$–$C_4$ alkyl, alkoxy or hydroxyalkyl, or polyalkyleneoxy groups.

The alkyleneoxy groups are preferably polyethyleneoxy groups or polypropyleneoxy or mixed ethyleneoxy propyleneoxy groups containing between 1 and 20 ethyleneoxy and/or propyleneoxy groups. The amidoalkyl groups are preferably $C_7$–$C_{23}$ alkyl or alkenyl-amidopropyl groups.

The amines may alternatively comprise cyclic amines such as imidazolines or pyridines, N-substituted piperazines, or N-substituted morpholines, e.g. N-methyl morpholine.

The process of this invention is typically carried out in aqueous solution. Optionally, a non phosphonate sequestrant such as EDTA may be used in the preparation which prevents decomposition of the hydrogen peroxide by chelating the metal ions which catalyse its decomposition. Alternative sequestrants include other chelating agents such as pyrophosphate. We prefer that such transition metal chelants or sequestrants should be present if the phosphonate is added after the commencement of the preparation. They accelerate the reaction but do not have any significant effect on the nitrosamine levels.

The required concentration of product depends on the particular tertiary amine starting material employed, since those that are preferred for this invention give rise to oxide products with surfactant properties which form a mobile $L_1$ phase at concentrations up to about 30% by weight based on total weight of reaction mixture, subject to exact chemical nature. At higher concentrations the amine oxide products tend to form an immobile M phase. Preferably, water is added to the reaction vessel in the form of aqueous hydrogen peroxide such that the final concentration of product attained is mobile. It is possible at high concentrations, e.g. 60 to 80% amine oxide (by weight based on total weight of reaction mixture) to form a mobile G phase. This option is, however, often impractical in a commercial scale manufacture due to the relatively narrow range of concentration over which the G-phase is usually obtained and consequently the most preferred embodiment is usually the most concentrated $L_1$ phase attainable, usually about 30% by weight based on total weight of reaction mixture. Higher concentrations may be achieved in the presence of phase modifiers such as solvents, cosurfactants, hydrotropes or electrolyte salts. These may raise the $L_1$/M boundary or broaden the G-phase range. The product may be prepared as anhydrous solid or as a solid hydrate. On a large scale, temperature rise may be a problem during the reaction, as conditions become closer to adiabatic, hence the use of a heel of amine oxide product is preferable since this limits the extent of the exotherm, by avoiding the induction period as the system passes from 2 phase to 1 phase.

The inventors have found that, in the presence of bicarbonate and/or carbonate in the proportions specified above, with or without phosphonate, careful control of temperature need not be such a crucial factor in limiting the formation of nitrosamines as by-products as is implied by the prior art, wherein it is stated (e.g. European Patent Application 88306270.3) that in order to inhibit the formation of nitrosamines the preparation of amine oxide must be conducted at 45° C. or lower; most preferably below 30° C. This then necessitates the usage of promoter to raise the slow reaction rate.

According to the present invention the inhibitory action of the stabiliser towards nitrosamine formation, reduces the importance of keeping the temperature low, during the preparation and/or the storage of amine oxides. Accordingly, the temperature of the reaction vessel when carrying out the process of this invention with the carbonate present initially may range from 2° C. to 85° C. but could be higher e.g. by carrying out the reaction in an autoclave to obtain very rapid reaction rates, the most preferred temperature range being 30° C. to 50° C. and a typical operating temperature being 40° C. The time to completion of the reaction is generally up to four hours.

Similarly, incorporation of the synergistic stabiliser, according to the invention, into an existing product renders it heat resistant with respect to the formation of nitrosamine impurities. The inventors have found that this effect is apparent even when the above mentioned product was not originally made in the presence of a nitrosamine inhibitor.

The amine oxide may be prepared, according to the present invention, by reacting a tertiary amine with hydrogen peroxide in the presence of the synergistic stabiliser hereinabove described.

The post addition of the poly(alkyleneamino) poly(methylenephosphonates) has been found to be advantageous in stabilising amine oxides generally, including those prepared by prior art methods, even in the absence of carbonate or bicarbonate. Compared with prior art methods in which the amino phosphonates were used to catalyse the preparation of the amine oxide and were necessarily converted to N-oxides in situ, the post addition does not result in the oxidation of the amine groups of the phosphonate. The resulting mixture of amine oxide and unoxidised poly(alkyleneamino) poly-(methylenephosphonate) is thus a novel and surprisingly advantageous composition which constitutes a particular aspect of the present invention. The mixture preferably comprises water, 10 to 99% preferably 15 to 85%, e.g. 20 to 35%, amine oxide and 0,005 to 5% especially 0.01 to 1% of the phosphonate all based on the weight of the composition. The phosphonate preferably comprises 1 to 6 preferably 2 to 5 ethylene and/or propylene groups. Optionally the composition may contain a quantity of amine oxide between 50 and 80% corresponding to that at which a G-phase is formed. Alternatively the concentration may be between 20% and the concentration corresponding to the $L_1$/M phase boundary, which is typically between 30% and 35%. Phase modifiers such as solvents, cosurfactants, hydrotropes or electrolyte salts, may raise the concentration of surfactant required to form an M-phase, so that the $L_1$/M phase boundary is found at concentrations of surfactant greater than 35% w/w. Addition of such phase modifiers may also broaden the concentration range over which the G-phase is typically found. It is also possible to prepare the amine oxide as a substantially anhydrous solid, or as a solid hydrate.

The invention may also be applicable to inhibition of nitrosamine and nitrite formation in the context of other reactions and products which involve a nitrosamine and nitrite hazard, for example alkanolamides.

The invention will be further illustrated by the following Examples in which all percentages are by weight based on the total weight of the product or reaction mixture as appropriate except where the context requires otherwise:

The examples 2 and 3 and 5 were based on the following typical preparative method:

Lauryl myristyl amine, as EMPIGEN AB (EMPIGEN is a Registered Trade Mark) was weighed into a flask with any required stabiliser and any required catalyst and the necessary quantity of water. The resulting mixture was warmed in a water bath to 65° C. with stirring for examples 2 and 3, and to 40° C. with stirring for example 5. 20% w/w of the total mass of hydrogen peroxide (35%) required was added to the abovementioned reaction mixture and the mixture allowed to stir for 30 minutes in order to overcome the reaction exotherm. After this time, the remaining quantity of hydrogen peroxide (35%) was added to the flask over 30–45 minutes and the reaction allowed to continue for approximately a further two hours, or until such time that it was determined the reaction had gone to completion.

In this instance, the reaction was deemed to have gone to completion when the free amine content of the reaction mixture was ≦0.3% w/w and the hydrogen peroxide content of the reaction mixture was ≦0.1% w/w, based on the total weight of the reaction mixture. If analysis of a reaction mixture aliquot showed a high free amine content but a low hydrogen peroxide content, more hydrogen peroxide was added and the reaction allowed to proceed until such time that acceptable levels of hydrogen peroxide and free amine content were achieved. Thus, in some instances, the ratio for moles (amine: $H_2O_2$) may be in excess of (1:1).

EXAMPLE 1

An unstabilised batch of lauryl myristyl amine oxide containing 30% by weight of the amine oxide 0.1% EDTA and 1176 ppb nitrosamine was mixed with the reagents shown below in Table 1. Samples were stored for two weeks at 70° C. and analysed by a chemiluminescence method for total "NO" content, after destruction of nitrite with sulphamic acid.

TABLE 1

TWO WEEK, 70° C. STORAGE TEST
WITH POST ADDED STABILISER

| Phosphonate | 0% | 0.01% | | 0.1% | 0.5% |
|---|---|---|---|---|---|
| "NO" ppb | 10,105 | 3,987 | | 2,533 | 2,792 |
| "NO" as % control | — | 39% | | 25% | 28% |
| Phosphonate | 0% | 0% | 0% | 0.01% | 0.1% | 0.5% |
| NaHCO$_3$ | 0% | 2% | 3% | 2% | 2% | 2% |
| "NO" ppb | 10,105 | 6,366 | 7,207 | 2,170 | 1,815 | 688 |
| "NO" as % control | — | 63% | 70% | 21% | 18% | 7% |

The phosphonate used in this and the following Tables was 25% w/w (expressed as acid) diethylenetriamine penta (methylenephosphonic acid) sodium salt-sold by Albright &

Wilson Ltd. under the Registered Trade Mark BRIQUEST 543-25S. The figures in the Tables for % phosphonate are all expressed as 100% acid.

Conclusions

The results show that the minimum level of nitrosamine that can be achieved by bicarbonate alone under the conditions of this experiment is 63% of the control even at high concentrations of stabiliser. Phosphonate alone cannot reduce the nitrosamine to less than 25% of the control.

A combination of 0.5% phosphonate +2% $NaHCO_3$ reduces nitrosamine to 7% of the concentration in the control and is thus responsible for a synergistic reduction in the "NO" content on ageing, when compared with unaged starting material, being more effective than the maximum achievable with either material on its own.

Example 2

An amine oxide was prepared using de-ionised water with the additions shown below in Table 2.

Both nitrite and nitrosamines were determined by chemiluminescence and are both quoted as "NO".

TABLE 2

TWO WEEK, 70° C. STORAGE TEST
WITH PRE ADDED STABILISER

| Reaction | A | B | C |
|---|---|---|---|
| Reaction time | 3 hours | 56.5 hours | 38 hours |
| Phosphonate (as acid) | 0.1% | — | 0.1% |
| $NaHCO_3$ | 1.0% | 1.0% | — |
| Nitrosamine ppb "NO" start | 51 | 171 | 240 |
| Nitrosamine ppb "NO" 2 weeks at 70° C. | 170 | 804 | 422 |
| $NO_2$ (as ppb "NO") start | 4,376 | 15,648 | 17,386 |
| Moles of (amine: $H_2O_2$) | (1:1) | (1:1.4) | (1:1.02) |
| Free amine levels (% w/w) at reaction completion | 0.1% | 0.3% | 0.3% |
| Peroxide residue (% w/w) at reaction completion | 0.024% | 0.01% | 0.08% |

The combination of phosphonate and $NaHCO_3$ gives reduced initial nitrosamine and nitrite levels, and reduces the formation of these during ageing at 70° C. Additionally the reaction time is appreciably reduced.

Example 3

Further reactions were run at 65° C. using water containing up to 5 ppm of Fe (II), distilled water, the results being shown below in Table 3. Iron is a notorious promoter of nitrosamine formation in amine oxides. Moreover in the absence of chelant 5 ppm iron prevents the reaction from proceding to completion due to decomposition of peroxide.

TABLE 3

TWO WEEK, 70° C. STORAGE TEST FOR SAMPLES
CONTAINING IRON CONTAMINATED WATER

| Reaction | A | B |
|---|---|---|
| Reaction time | 40 hours | 2 hours |
| Phosphonate (as acid) | 0.1% | 0.1% |
| $NaHCO_3$ | — | 1.0% |
| "NO" ppb start | 162 | 34 |
| "NO" ppb 2 weeks at 70° C. | 3,940 | 269 |
| $NO_2$ (as ppb "NO") start | 15,465 | 2,670 |
| Moles of (amine: $H_2O_2$) | (1:1.03) | (1:1) |

TABLE 3-continued

TWO WEEK, 70° C. STORAGE TEST FOR SAMPLES
CONTAINING IRON CONTAMINATED WATER

| Reaction | A | B |
|---|---|---|
| Free amine levels (% w/w) at reaction completion | 0.3% | 0.3% |
| Peroxide residue (% w/w) at reaction completion | 0.06% | 0.025% |

The above results demonstrate the superiority of a combination of $NaHCO_3$ and phosphonate, as a catalyst for the reaction and as an inhibitor for $NO/NO_2$ formation both during the reaction and on ageing, even in the presence of iron.

Example 4

The products of reactions A and B, shown above in Table 3, were each dosed, after preparation, with extra phosphonate as shown below in Table 4, (both had 0.1% phosphonate in the reaction charge).

TABLE 4

TWO WEEK, 70° C. STORAGE TEST TO SHOW THE
EFFECT OF POST ADDITION OF FURTHER
QUANTITIES OF STABILISER

|  | A | B | C | D | E |
|---|---|---|---|---|---|
| Reaction A + phosphonate | — | 0.1% | 0.3% | 0.4% | (CONTROL)* |
| "NO" ppb Start | 162 |  |  |  | 182 |
| "NO" ppb 2 weeks at 70° C. | 3940 | 855 | 560 | 520 | 3753 |

*Prepared in a similar way to Reaction A but with 0.5% phosphonate (as acid) included in the reaction.

| Reaction B + phosphonate | — | 0.1% | 0.3% | 0.4% | (CONTROL)* |
|---|---|---|---|---|---|
| "NO" ppb Start | 34 |  |  |  | 39 |
| "NO" ppb 2 weeks at 70° C. | 269 | 92 | 109 | 102 | 125 |

*Prepared in a similar way to Reaction B but with 0.5% phosphonate (as acid) included in the reaction.

Conclusions

Post addition of further phosphonate, as in reaction B,C and D, is more effective in lowering the total nitrosamine and nitrite content of the samples, than is achieved by initially adding the total amount of stabiliser to the reaction mixture. Thus, the stabilising effect is maximised by post addition of further phosphonate.

It should be appreciated that all of the 70° C. two week storage tests hereinabove described are conducted in considerably harsher conditions than are typically encountered in practice, in order to demonstrate significant differences within a short period. Usually storage temperatures are in the range of 20° to 45° C., which promotes the formation of nitrosamines and nitrites to a lesser extent than a storage temperature of 70° C., and thus represents a more industrially relevant study.

Example 5

Two further samples (A and B), of amine oxides were prepared using ultra high purity water, with the additions shown below in Table 5 made at the start of the reaction.

Another batch of amine oxide (C) received a post addition of phosphonate.

Both nitrite and nitrosamines were determined by chemiluminescence and both are quoted as "NO".

TABLE 5

TWO WEEK, 45° C. STORAGE TESTS

| Reaction | | A | B | C |
|---|---|---|---|---|
| Phosphonate | | | 0.25% | |
| E.D.T.A. | | 0.1% | | 0.1% |
| Sodium Bicarbonate | | 1.0% | 1.0% | 1% |
| Phosphonate (post addition) | | | | 0.25% |

| sample | | start | 14 days | 28 days | 42 days | 56 days |
|---|---|---|---|---|---|---|
| A | ppb nitrosamines | 22 | | 68 | 71 | 155 |
|   | ppb nitrite | 428 | | 770 | 843 | 1210 |
| B | ppb nitrosamines | <10 | | 20 | 23 | 36 |
|   | ppb nitrite | 183 | | 483 | 665 | 759 |
| C | ppb nitrosamines | 12 | <10 | | 18 | |
|   | ppb nitrite | 443 | 338 | | 429 | |

Conclusion

The post addition of phosphonate to sample (C) provides improved inhibition of nitrosamine and nitrite levels on storage at 45° C., illustrating the synergistic effect of phosphonate (post addition) and bicarbonate. The beneficial effect of using phosphonate in preference to E.D.T.A. is seen by comparison of samples A and B.

We claim:

1. A composition comprising an amine oxide and a synergistic stabiliser therefore wherein said stabiliser comprises:
   (i) from 0.05% to 20% by weight based on the weight of the amine oxide of a material selected from the group consisting of bicarbonates, carbonates and mixtures of said bicarbonates and said carbonates; together with
   (ii) from 0.005% to 5% by weight based on the weight of the amine oxide of a phosphonate; and
   said amine oxide is an oxide of an amine of formula $R^1R^2R^3N$ wherein $R^1$, $R^2$ and $R^3$ are each selected from the group consisting of straight or branched chain alkyl, straight or branched chain alkenyl, aralkyl, $C_{6-24}$ alkyl polyalkleneoxy, $C_{6-24}$ alkenyl polyalkyleneoxy, $C_{6-23}$ esteralkyl and $C_{6-23}$ esteralkenyl groups and wherein $R^1$ and $R^2$ can form a heterocyclic ring.

2. The composition of claim 1 wherein said phosphonate (ii) is selected from the group consisting of aminophosphonates and aminophosphonate N-oxides.

3. The composition of claim 2 wherein said phosphonate (ii) is selected from the group consisting of poly(alkyleneamino) poly(methylenephosphonate) and N-oxides thereof.

4. The composition of claim 3 wherein said alkyleneamino groups are selected from ethyleneamino groups and propylene amino groups.

5. The composition of claim 4 wherein said phosphonate includes from 2 to 6 alkyleneamino groups selected from ethyleneamino, propyleneamino and mixtures of said ethyleneamino and propyleneamino groups.

6. The composition of claim 1 wherein (ii) is selected from the group consisting of diethylenetriamine pentakis(methylenephosphonate), triethylenetetramine hexakis(methylenephosphonate) and tetraethylenepentamine heptakis(methylenephosphonate).

7. The composition of claim 1 comprising said amine oxide and from 0.05 to 5% (based on the weight of said amine oxide) of a non-oxidised poly(ethyleneamino) poly(methylenephosphonate).

8. The composition of claim 7 wherein said amine oxide is selected from the group consisting of solid amine oxides and amine oxide hydrates.

9. The composition of claim 1 or claim 8 comprising water and from 10 to 99% by weight of said composition of said amine oxide.

10. The composition of claim 9 wherein said amine oxide is present as a G-phase.

11. The composition of claim 9 wherein said amine oxide is present as an $L_1$ phase.

12. The composition of claim 11, said composition contains at least 20% by weight of said amine oxide.

13. The composition of claim 1 wherein said amine oxide is an oxide of an amine of formula $R^1R^2R^3N$ wherein $R^1$, $R^2$ and $R^3$ are each selected from the group consisting of straight or branched chain alkyl, straight or branched chain alkenyl, $C_{6-24}$ alkyl polyalkleneoxy, $C_{6-24}$ alkenyl polyalkyleneoxy, $C_{6-23}$ esteralkyl and $C_{6-23}$ esteralkenyl groups.

14. The composition of claim 13 wherein the polyalkylene oxide group is polyethylene oxide group, polypropylene oxide or a combination thereof.

15. The composition of claim 1 wherein said amine oxide is an oxide of an amine selected from the group consisting of imidazolines, pyridines, N-substituted piperazines and N-substituted morpholines.

16. The composition of claim 1 wherein (i) is selected from the group consisting of alkali metal bicarbonates and alkaline-earth metal bicarbonates.

17. The composition of claim 1, wherein (i) is selected from the group consisting of alkali metal carbonates, alkaline-earth metal carbonates and ammonium carbonate.

18. The composition of claim 1, wherein (i) consists essentially of a mixture of sodium bicarbonate and sodium carbonate.

19. The composition of claim 1, wherein the weight ratio of said carbonate to said bicarbonate is from 0.01:1 to 1:0.01.

20. The composition of claim 1, wherein (ii) comprises a material chosen from the group consisting of amino tris(methylenephosphonate), ethylenediamine tetrakis(methylenephosphonate), diethylenetriamine penta(methylenephosphonate), triethylenetetramine hexa(methylenephosphonate), tetraethylenepentamine hepta(methylenephosphonate) and oxides of any of said phosphonates.

* * * * *